United States Patent [19]

Caprino

[11] 3,966,915

[45] June 29, 1976

[54] TREATMENT OF HEART DISEASES

[75] Inventor: Luciano Caprino, Rome, Italy

[73] Assignee: Istituto Farmacologico Serono S.p.A., Rome, Italy

[22] Filed: June 19, 1974

[21] Appl. No.: 480,746

Related U.S. Application Data

[63] Continuation of Ser. No. 324,572, Jan. 18, 1973, abandoned.

[30] Foreign Application Priority Data

Feb. 11, 1972 Italy .................................. 48280/72

[52] U.S. Cl. ................................... 424/177; 424/95
[51] Int. Cl.² ......................................... A61K 37/00
[58] Field of Search ............................. 424/177, 95

[56] References Cited
OTHER PUBLICATIONS

Chemical Abstracts 58:7263a, (1963).

Primary Examiner—Leonard Schenkman
Attorney, Agent, or Firm—Ostrolenk, Faber, Gerb & Soffen

[57] ABSTRACT

Phosvitin, a phosphoprotein extracted from hen's egg yolk, has been found effective in the treatment of such heart diseases as myocardial diseases, coronary heart diseases and heart failure.

6 Claims, No Drawings

TREATMENT OF HEART DISEASES

This is a continuation of application Ser. No. 324,572, filed Jan. 18, 1973, now abandoned.

BACKGROUND OF THE INVENTION

This invention relates to medicaments and, more particularly, to the therapeutical use of a phosphoprotein existing in nature which is called "Phosvitin". Since 1885 Bunge (Z. Physiol. Chem. 9,49:1885) isolated from egg yolk an iron-containing phosphoprotein complex. A few years after, Huguenenq and Morel (Compt. Rend. 140, 1065; 1905) expressed the hypothesis that such complex — which was named by them "haemotogen"—would be involved in the formation of the fowl embryo haemoglobin. This substance awakened the interest of many scientists; however, only in 1949 Mecham and Olcott (J. Am. Chem. Soc. 71, 3670; 1949) were able to isolate from egg yolk a homogenous phosphoprotein fraction that was named by them "Phosvitin". The identity of the former "haemotogen" with such "iron-phosvitin"complex was demonstrated in 1964 by O. Greengard et al. (Biochim. Biophys. Acta 90, 406, 1964).

The presence of phosvitin having been shown in the hen's egg, an obvious consequence was that it was sought for in the eggs of other animals; in fact, Wallace et al. (Canad. J. Biochem. 44, 1647; 1966) isolated it from the eggs of vertebrata (tortoise, frog and so on); G. Schmidt et al. (Biochem. Biophys Research Communications 18, 60, 1965) from the eggs of salmon; and Y. Macco et al. (J. Biol. Chem. 241, 3822; 1966) from the eggs of certain species of fish.

Further and deeper investigation was devoted to seek for phosvitin in the blood of hen and other animals, since it was logical to suppose that its synthesis would occur in some organ and that phosvitin would be transferred from such organ to the egg yolk through the blood flow. Thus, Mock et al. (Canad. J. Biochem. Physiol. 39,109; 1961) extracted phosvitin from the blood of non-laying hens to which estrogens had been administered, whereas Heald et al. (Biochem. J. 87, 571; 1963) demonstrated that a substance identical to the phosvitin existing in the egg yolk can be found in the blood of laying hens, even if the latter have not been treated with estrogens. Further studies showed that phosvitin is synthesized in the liver and that its formation is hormone-controlled, since it is stimulated by the presence of estrogens.

From the chemical point of view, phosvitin is a phosphoprotein, that is, a protein containing removable phosphate groups which can be easily removed by treatment with alkali and enzymes (phosphokinase).

In its molecule, 17 amino acids have been identified, 50% of which is serine; hexoses (about 2.5%) and glucosamine (1.4%) are also present. The estimated molecular weight is about 40,000 to 50,000 (Allerton et al., J. Biol. Chem. 240,3892; 1965).

In the lyophilized state, phosvitin appears as an off-white odorless powder which is soluble in water, 0.9% saline and 10% $MgSO_4$ solution, whereas it is insoluble in a solution containing less than 2.5% $MgSO_4$ and in the usual organic solvents. Isoelectric point = pH 1.8.

Phosvitin contains 9.6 ± 0.3% phosphorus, 11.6 ± 0.4% nitrogen and 0.3 to 0.4% iron. Molar ratio P/N=2.5 to 2.9; ashes = 31 ± 2%.

A solution containing 0.16% phosvitin in 0.1 M potassium chloride at pH 6.5 to 6.7 has no significant absorption peak between $\lambda = 250$ and $\lambda = 290$ millimicrons. Paper electrophoresis (Whatman 3 MM strips; 3×27 cm; 200 v-10 mA) of 0.3% phosvitin in borate buffer shows a spot only using the reagent specific to phosphate esters (blue spot), whereas Schwarz starch, that is a reagent specific to proteins, does not show any further spots. A further characteristic feature is that when treated with 1% toluidine blue in 7% acetic acid the paper strip shows a blue coloured spot which does not disappear when dipped in 7% acetic acid methanol solution.

By the usual procedure of polyacrylamide gel electrophoresis, phosvitin gives one or more blue bands (which are due to the formation of molecular aggregations) when treated with 1% toluidine blue in 7% acetic acid.

By column chromatography on DEAE-cellulose, phosvitin is eluted as a single homogenous fraction.

From the above it clearly appears that phosvitin is a known substance which has been extensively studied by a number of investigators. However, no pharmacological-therapeutical actions of this substance have been disclosed.

SUMMARY OF THE INVENTION

Surprisingly, the investigation carried out by the Applicant has shown that phosvitin is a medicament particularly suitable for use in treating such diseases as myocardial (in particular dysmetabolic myocardial) diseases and coronary heart diseases, as well as for use as adjuvant in treating heart failure.

Therefore, the invention provides a new medicament for the treatment of the above diseases, pharmaceutical preparations comprising of the above new medicament together with compatible and pharmaceutically acceptable excipients and/or carriers, as well as a method for treating the said diseases consisting in administering to a man and/or animal a therapeutically effective dose of the said new medicament or pharmaceutical preparations. Further aspects of the invention will become apparent to a skilled person from the following description and illustration.

DETAILED DESCRIPTION OF THE INVENTION

The acute toxicity of the new medicament of this invention was determined in the mouse intravenously, intraperotoneally and orally. The tests carried out on adult male Swiss mice having the average weight of 18 g. gave the following results:

$LD_{50}$ = 334.41    mg/kg i.v.
$LD_{50}$ = 4050      mg/kg i.p.
$LD_{50}$ > 8000      mg/kg orally The following Examples illustrate the invention.

EXAMPLE 1

Male albino Wistar rats having the average weight of 240 g. were first anaesthetized with 35 mg/kg i.p. sodium pentobarbital (Nembutal) and treated with 2 I.U./kg vasopressin (Pitressin) by quick intravenous infusion, then given phosvitin at doses of 1000 mg/kg i.p. or 750 mg/kg i.p. plus 250 mg/kg i.v.

In both cases, a marked reduction or prevention of the main electrocardiographic changes induced by the intravenous administration of vasopressin was observed.

EXAMPLE 2

Male albino Wistar rats having the average weight of 240 g. were first put in hypoxia by forced ventilation of an air/nitrogen mixture (30:70 by volume) and treated with 2–3 mcg./kg i.v. nor-adrenaline, then given phosvitin at the dose of 1000 mg/kg i.p.

A marked reduction or prevention of the main electrocardiographic changes induced by the intravenous administration of nor-adrenaline to animals put in hypoxia was observed.

EXAMPLE 3

A guinea-pig isolated atrium dipped in Ringer-Krebs-Henselait solution was made hypodynamic by submitting it to prolonged electric stimulation at the constant frequency of 2 stimuli per second (5 milliseconds per stimulus).

The increase of contraction amplitude induced by the addition of 1 mcg. per ml. bath of either nor-adrenaline or adrenaline was markedly enhanced in both cases by the addition of phosvitin at the dose of 25 mcg/ml bath.

Further experiments showed that the new medicament of the invention lacks any coronarodilator activity.

From the above it clearly appears that phosvitin is a highly useful therapeutical means in myocardial (in particular dysmetabolic myocardial) diseases, in coronary heart diseases and as adjuvant in heart failure.

A typical preparation of phosvitin by extraction from hen's egg yolk is as follows.

Eggs were broken, yolk was separated from albumen and extracted several times with ethanol. The alcoholic phospholipid-containing liquor was put aside whereas the protein residue was squeezed and extracted several times with acetone. The acetonic neutral fat (egg oil) — containing liquor was put aside whereas the protein residue, deprived both of phospholipids and lipids, was extracted with 10% magnesium sulfate aqueous solution. Raw phosvitin was precipitated by diluting the saline solution with 3.4 volumes of water and dissolved in 10% sodium chloride aqueous solution. Further magnesium sulfate was added up to 10% concentration, the saline was filtered and phosvitin was precipitated again by diluting with 3.4 volumes of water. The obtained phosvitin precipitate was first dissolved in 10% NaCl, then desalinated through dialysis, filtered and lyophilized.

Lyophilized phosvitin is usually mixed with such suitable excipients as mannose, lactose and glycocoll in a weight ratio phosvitin: excipient generally ranging from 1:1 to 1:0.1. In accordance with the invention it has been found that, among the excipients, glycocoll particularly helps solution of the lyophilized product in water or saline.

For this purpose the preferred phosvitin: glycocoll ratio is of about 1:0.5. Therefore, a preferred aspect of the invention relates to a pharmaceutical preparation in lyophilized form containing phosvitin and glycocoll in a ration of about 1:0.5 as well as a common antiseptic agent such as, for example, sodium thimerosal (Merthiolate).

The following is a typical example of preparing ampoules or vials containing a pharmaceutical preparation in lyophilized form according to the invention.

EXAMPLE 4

An aqueous solution was prepared having the following composition:

| | |
|---|---|
| Phosvitin | 10 g. |
| Glycocoll | 5 g. |
| Sodium Merthiolate | 10 mg. |
| Apyrogenic distilled water up to 100 ml. | |

The above ingredients were dissolved at room temperature (22° to 25°C) under stirring. The obtained solution was filtered through sterilising SEITZ EK filter and put into 3 ml. dark-glass ampules or vials in the amount of 1 ml. per each ampule or vial. Freezing and lyophilization were carried out subsequently. Therefore, each ampule or vial of lyophilized product contained 100 mg. phosvitin and 50 mg. glycocoll.

A pharmaceutically effective daily dose in man has been found to be in a range of about 0.1 to 1 g. phosvitin. A preferred way of administration is by intramuscular or intravenous injection.

What we claim is:

1. A method for the treatment of heart disease by increasing the contraction amplitude of the heart which comprises administering to man a pharmaceutically effective amount of about 0.1 to 1 gram per day of phosvitin.

2. The method of claim 1 in which the phosvitin is administered by injection.

3. The method of claim 1 in which phosvitin is administered in combination with a pharmaceutically acceptable carrier or diluent.

4. The method of claim 3 in which the phosvitin is administered by injection.

5. The method of claim 3 in which phosvitin is administered in combination with glycocoll.

6. The method of claim 5 in which the phosvitin is administered by injection.

* * * * *